United States Patent [19]

Kawa

[11] Patent Number: 5,455,373

[45] Date of Patent: Oct. 3, 1995

[54] METHOD OF PRODUCING PERFLUOROCARBON HALIDES

[75] Inventor: Hajimu Kawa, Austin, Tex.

[73] Assignee: Exfluor Research Corporation, Austin, Tex.

[21] Appl. No.: 202,917

[22] Filed: Feb. 28, 1994

[51] Int. Cl.⁶ .......................... C07C 53/15; C07C 71/00
[52] U.S. Cl. .................. 560/300; 560/227; 562/125; 562/550; 554/129; 558/243; 558/249
[58] Field of Search ................... 560/300, 227; 562/125, 550; 554/129; 558/243, 249

[56] References Cited

U.S. PATENT DOCUMENTS

| | | | |
|---|---|---|---|
| 3,790,607 | 2/1974 | Lichstein | 554/129 |
| 3,979,469 | 9/1976 | Jager | 554/129 |
| 4,098,806 | 7/1978 | Commeyras et al. | 554/129 |

*Primary Examiner*—Arthur C. Prescott
*Attorney, Agent, or Firm*—Lahive & Cockfield

[57] ABSTRACT

A method of producing perfluorocarbon halides in a one-pot reaction is described. The method employs a perfluorocarbon acid, a first halogenating agent and a second halogen which drives the reaction forward. Novel perfluorocarbon halides and a direct method for producing perfluorocarbon hypohalites also are described.

24 Claims, No Drawings

METHOD OF PRODUCING PERFLUOROCARBON HALIDES

BACKGROUND OF THE INVENTION

Perfluoroalkyl bromides have been developed as non-toxic contrast agents which can function as synthetic oxygen carriers. Properties of perfluoroalkyl bromides which render them desirable in various biomedical applications include their non-toxicity, their stability in emulsions at relatively high concentrations and their relatively high vapor pressure. These properties allow perfluoroalkyl bromides to be eliminated expediently from a subject's body after intravascular administration. Preferred perfluoroalkyl bromides for biomedical applications include perfluorooctyl bromide (PFOB) and perfluorodecalin (PFD). PFOB-based emulsions are used often because of their stability at high concentrations and ability to be rapidly transported to and excreted from tissues.

However, even PFOB-based emulsions suffer some disadvantages and limitations. Various biomedical applications require the use of fluorocarbon fluids which have a shorter residence time within a patient and thus have even higher vapor pressures than that of PFOB. Further, the need exists for a fluorocarbon fluid which can be administered in even higher concentrations and lower volumes than those which are possible with PFOB. Finally, existing methods for making perfluoroalkyl bromides are inefficient and costly.

Perfluoroalkyl halides are generally produced in a two-step reaction between a perfluorocarbon acid and silver salts using a Hunsdiecker reaction, as shown below (see Haszeldine, R. N., *The Reactions of Metal Salts of Acids With Halogens. Part III. Some Reactions of Salts of Fluorohalogenoacetates and of Perfluoro-acids*, J. Chem. Soc. 4259 (1952)).

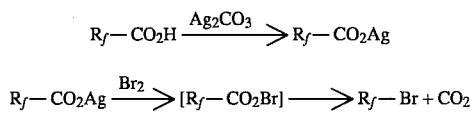

The product of the first reaction step is an intermediate compound, perfluoroalkyl hypohalite, which immediately decomposes to a perfluoroalkyl halide and carbon dioxide accompanied by a release of free radicals. For example, in the Hunsdiecker reaction a perfluorocarboxylic acid reacts with silver carbonate to form perfluoro silver acetate ($R_f$—$CO_2Ag$). This first reaction product is then purified in the presence of bromine to form the unstable intermediate compound, perfluoroalkyl hypobromite ($R_f$—$CO_2Br$), which then decomposes to perfluoroalkyl bromide and carbon dioxide. Disadvantages of this method include the use of relatively expensive and potentially biohazardous silver salts, the inefficiencies associated with the indirect production of the desired perfluoroalkyl halide compound, and an inability to control, e.g., thermodynamically, the reaction. This lack of control arises from the extreme reactivity of the $R_f$ radical with halogenating compounds, e.g., Br, which is important in determining specific yields of the perfluoroalkyl halide. Although less expensive Group I metals, including sodium and potassium, have been used in place of silver, the results and yields have still been unsatisfactory.

SUMMARY OF THE INVENTION

This invention provides methods of producing perfluorocarbon halides, e.g. perfluoroalkyl halides, that are non-toxic, highly stable in emulsions, have a relatively high vapor pressure, and which can be administered in relatively high concentrations and in low volumes to a patient. The methods of this invention are commercially feasible for large scale production of perfluoroalkyl halides. This invention is based, at least in part, on the discovery that perfluorocarbon halides can be formed in a one pot reaction from a perfluorocarbon acid, a first halogenating agent and a second halogen which drives the reaction. The formation of the perfluorocarbon halide of the present invention can be advantageous over conventional approaches because this particular combination allows for the direct formation of a perfluorocarbon hypohalite intermediate compound which then decomposes into the perfluorcarbon halide in a one pot reaction.

Other aspects of this invention include perfluorocarbon halides produced by the present methods, novel perfluorocarbon halides and compositions and/or emulsions containing these halides. The compositions and/or emulsions can be used in the biomedical fields for both therapeutic and diagnostic purposes.

DETAILED DESCRIPTION

The present invention provides a method of producing a perfluorocarbon halide. The method involves contacting a perfluorocarbon acid with a first halogenating agent in the presence of a second halogen. The second halogen is selected to drive the reaction such that a perfluorocarbon halide is formed.

The language "perfluorocarbon halide" is intended to include halogenated compound(s) having a perfluorinated hydrocarbon moiety wherein at least two of the hydrogen atoms along the hydrocarbon moiety have been replaced with fluorine atoms. It should be understood that a substantial portion of the hydrogen atoms can be replaced with fluorine atoms, e.g., the entire moiety can be completely perfluorinated. All degrees of perfluorination along the hydrocarbon moiety are intended to be part of this invention.

The language "perfluorinated hydrocarbon moiety" is perfluorinated as described above and intended to include substituted and unsubstituted alkyl, alkenyl, alkynyl, alkoxyl groups which can have straight or branched chains. The hydrocarbon moiety further can include or be a ring structure including single or fused ring structures, e.g., phenyl, or naphthyl. The unsaturated groups can have a single site of unsaturation or a plurality of sites of unsaturation. The substituents on the hydrocarbon moiety can be on a side chain extending from the hydrocarbon backbone or can be a substituent(s) located within the hydrocarbon backbone, e.g., forming an ether linkage or even a peroxide. The substituents are selected such that their presence on the hydrocarbon moiety does not detrimental effect the ability of the halogenating agent to halogenate the perfluorocarbon acid. Examples of such substituents include hetero atoms, e.g., oxygen, sulfur, and nitrogen. The hydrocarbon groups preferably contain up to about twenty carbon atoms, more preferably up to about fifteen carbons, and most preferably up to about ten carbons. Specific perfluorocarbon halides produced of this invention are described in the examples below and further include bromofluorohexane, e.g., 1-bromoperfluorohexane, ($BrCF_2CF_2CF_2CF_2CF_2CF_2$ Br) or 1,6-dibromoperfluorohexane ($CF_3CF_2CF_2CF_2CF_2CF_2Br$), bromofluoroheptane, e.g., 1-bromoperfluoroheptane, ($CF_3CF_2CF_2CF_2CF_2CF_2CF_2Br$), bromofluorooctane, e.g., 1-bromoperfluorooctane, ($CF_3CF_2CF_2CF_2CF_2CF_2CF_2CF_2Br$) or 1,8-dibromoperfluorooctane, ($BrCF_2CF_2CF_2CF_2CF_2CF_2CF_2CF_2Br$), bromofluorononane, e.g., 1-bromoperfluorononane, (CF$_3$CF$_2$CF$_2$CF$_2$CF$_2$CF$_2$CF$_2$CF$_2$Br), bromofluorobutane, e.g., 1,4-dibromoperfluorobutane, (BrCF$_2$CF$_2$CF$_2$CF$_2$Br).

The language "perfluorocarbon acid" is intended to include a hydrocarbon moiety as defined above having at least one acid group attached to or incorporated within the moiety. The acid can be a single acid or a polyacid having a plurality of acid groups attached throughout the hydrocarbon moiety. The acid group(s) can extend from a side chain of the hydrocarbon moiety or can extend directly from the backbone of the hydrocarbon moiety. The acid group(s) are placed such that halogenation of the groups occurs using the method of the present invention.

The preferred perfluorocarbon acid of this invention is encompassed by the formula (I) set forth below:

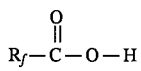

wherein R$_f$ is a perfluorinated hydrocarbon moiety as described above. Examples of lower molecular weight perfluorocarboxylic acids include formic, acetic, propianic, butyric, valeric, caproic, enanthric, caprylic, pelargonic, captic, isobutyric, benzoic, p-toluic, o-phthalic, cyclohexanecarboxylic, and acrylic acids. Additional examples include perfluorononanoic acid, perfluorooctanoic acid, perfluorodecanoic acid, perfluorododecanoic acid, perfluoro(decahydro-1-naphthoic acid), perfluoro(3,6,9-trioxaundecanoic acid), perfluoro-1,6-hexanedioic acid, perfluoro(4,7,10-trioxatridecane-1,1,3-dioic acid), perfluoro(3,7-dimethylheptanoic acid), and perfluoroheptanoic acid. Examples of lower molecular weight diacids include oxalic, malonic, succinic, glutaric, adipic, and pimelic.

The language "halogenating agent" is art-recognized and is intended to include agents which replace at least one of the hydrogen atoms in an acid group of the perfluorcarbon acid. Examples of halogenating agents include elemental bromine, elemental iodine, elemental chlorine, elemental fluorine, hydrobromic acid, hydroiodic acid, hydrochloric acid, potassium bromide, potassium iodide, potassium chloride, trimethylsilyl bromide, trimethylsilyl iodide, trimethylsilyl chloride, fluorocarbons, chlorofluoroethers, and derivative compounds thereof.

The term "halogen" is art-recognized. The halogens include those which drive the reaction towards the perfluorocarbon halide final product. Examples of such halogens include those capable of forming a strong hydrogen bond with a hydrogen released from an acid group. Specific examples include elemental fluorine, chlorine, bromine, or iodine. The form of the halogen is one which allows the halogen to perform its role within the methods of the invention. The halogen can be in its elemental form, e.g., elemental fluorine, chlorine, bromine, or iodine, or can be in other forms.

The term "perfluorocarbon hypohalite" is intended to encompass intermediates produced by the methods of this invention which differ from the perfluorocarbon acid(s) in that a hydrogen in at least one of the acid groups is replaced by a halogen atom. For example, the hypohalites of the compounds encompassed by formula (I) are as follows:

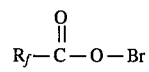

The reaction conditions (temperature, choice of solvent, order of reagents, reaction medium (liquid or solid), etc. of the methods of the present invention can vary based on many factors, e.g., the particular reagents employed, the desired final product, and the degree of fluorination of the starting material. The description of the preferred embodiment and the examples below provide some specific conditions for the methods of this invention. The below listed patents also provide information, e.g., reaction conditions, which can be useful for the present methods.

U.S. Pat. No. 5,093,432 of Bierschenk et al describes a method for liquid phase fluorination of a wide variety of hydrocarbons. The fluorination is performed in a perhalogenated liquid medium, such as a perfluorocarbon medium, a perhalogenated chlorofluorocarbon medium or a perhalogenated chlorofluoroether. The classes of materials that can be fluorinated are described to be alkanes, alkenes, aromatic hydrocarbons, sulfonic acid derivatives, amines, chlorinated hydrocarbons, carboxylic acid and derivatives thereof, ethers, formals, acetals, ketals, and epoxides. These reagents in a perfluorocarbon acid form along with the liquid phase fluorination teachings are incorporated by reference herein.

U.S. Pat. No. 4,859,747 of Bierschenk et al., U.S. Pat. No. 5,053,536 of Bierschenk et al., U.S. Pat. No. 5,075,509 of Lagow, U.S. Pat. No. 5,132, 455 of Lagow, U.S. Pat. No. 5,202,480 of Bierschenk et al., and U.S. Pat. No. 5,202,501 of Lagow et al., describe further methods for fluorinating hydrocarbons. For example, the '747 patent described methods for direct flourination of ethers in the presence of hydrogen fluoride scavengers; the '536 patent describes methods of fluorinating acetals, ketals, and orthoesters; and the '509 patent describes methods of fluorinating orthocarbonates and polyalkoxy propanes. The entire contents of the foregoing publications and patents, and any that appear hereinafter, are herein expressly incorporated by reference, along with their published foreign counterparts, unless expressly stated otherwise.

The Preferred Embodiment

The one-pot reaction of the present invention proceeds according to the following equation:

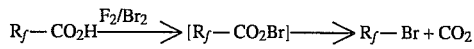

wherein Br$_2$ is a brominating agent.

When the perfluorocarboxylic acid is reacted with elemental fluorine in the presence of the brominating agent, such as bromine, bromine monofluoride (BrF) is readily formed. The reaction of bromine monofluoride with the perfluorocarboxylic acid produces a hypohalite intermediate compound and hydrogen fluoride (HF). The formation of a strong H-F bond drives the present reaction in the forward direction towards the desired end product. The hydrogen fluoride generated by the reaction can be removed from the reaction by well-known hydrogen fluoride scavengers, such as sodium fluoride and potassium fluoride. The hypohalite intermediate compound decomposes into a perfluoroalkyl halide and carbon dioxide (CO$_2$).

The perfluorocarboxylic acid can be dissolved in an optional solvent, or the perhalogenated compound can itself can function as the solvent along with the halogenating agent, as the reaction proceeds. The term "solvent" is intended to include liquid or gaseous mediums having solvating powers. The solvents include mediums which are non-reactive with halogen compounds while being capable of dissolving halogenating agents. Examples of solvents can include chloroform, trichloroethane, trichloroethene, trifluoroacetic acid, trifluoroacetic anhydride, 1,1,2 trichlorofluoroethane, elemental halogen compounds, perfluoroalkane, perfluorotrialkylamine, perfluoroether, chlorofluorocarbon, bromofluorocarbon, and fluorocarbons.

In an alternate embodiment, the fluorine and bromine can be premixed in a solvent to form an equilibrating mixture of bromine monofluoride (BrF) and bromine trifluoride (BrF$_3$), as shown by the following formula:

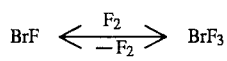

The perfluorocarboxylic acid can then be added directly to the mixture. The preferred halogen compound is flourine, and the preferred halogenating agent is bromine or other suitable brominating reagents.

The term "brominating reagents" is intended to include agents capable of imparting a bromine substituent to another compound or moiety. Examples of preferred brominating agents include elemental bromine, hydrogen bromide, potassium bromide and trimethylsilyl bromide.

The foregoing conversion reactions can be performed at various halogen concentrations, by contacting the halogen with a diluent, ranging from less than one percent halogen concentration to pure halogen (e.g., <1%–100%). The halogen concentration need not remain constant during the reaction.

The term "diluent" is intended to include any medium that would not produce a flammable mixture or compound when reacted with a mixture of a halocarbon, halogenating agent and halogen compound, and which does not individually react with halogens. Preferred diluents include nitrogen and other inert gases, which are art known, such as helium, neon and argon.

It is preferred to use an excess amount of fluorine and preferably an excessive amount, of a halogenating agent to increase the total yield of the resulting perfluoroalkyl halide. When less than stoichiometric amounts of fluorine and halogenating agent are used, the unreacted perfluorocarboxylic acid can be recovered from the reaction mixture by adding dilute hydrochloric acid (HCl) to the mixture, and by collecting the precipitated solids by known filtration techniques. Alternatively, when the perfluorocarboxylic acid is relatively soluble in the solvent, if used, an additional amount of the unreacted acid can be recovered as a residue from known distillation techniques.

The reaction temperatures of the above reaction mixtures can range between −20° C. and 100° C., and preferably between 0° C. and 50° C., to optimize the capture of halogen in the form of halogen monofluoride without exceeding the flashpoint of the solvent.

The present invention is further illustrated by the following non-limiting examples. All issued patents, published patent applications and publications cited throughout the present application are expressly incorporated by reference.

EXAMPLE 1—Preparation of Perfluorooctyl Bromide

Perfluorononanoic acid 100 g (0.215 mole), bromine 41 g (0.258 mole) and Freon 113 (500 ml) were mixed in a 2-liter Teflon plastic bottle. This plastic reactor was equipped with a Teflon-coated magnetic stir bar, inlet and outlet tubes made of Teflon-FEP, and a thermocouple coated with Teflon-FEP. The outlet tube was connected to a condensor which was chilled with an ethylene glycol-water mixture. The acid solution was warmed to 30 ° C. through agitation while the reactor was purged of air by flushing it with an inert gas, such as nitrogen, through the inlet tube; The nitrogen flow was terminated and fluorine gas was bubbled into the mixture at 30 cc/min. The fluorine, supplied by Air Products, was used without further purification. The fluorine flow rate was controlled with a Monel needle valve and monitored with a Hastings mass flow transducer. Despite an exothermic reaction occurring immediately, the reaction temperature was kept at 30°–40° C. throughout the reactor by external cooling. The fluorine flow was maintained until the color of the solution turned from deep red to light yellow. Approximately 2.2 fold excess of fluorine (based on the initial amount of acid used) was required to produce this result. After the fluorine gas was terminated, the reactor was again purged with nitrogen and the mixture was carefully poured into water. The organic precipitate was washed with water containing a small amount of sodium thiosulfite, and then dried over magnesium sulfate. Fractional distillation of the precipitate produced 100 grams of perfluorooctyl bromide (97% yield) having a boiling point between 142°–144° C.

EXAMPLE 2—Preparation of Perfluorooctyl Bromide

Perfluorononanoic acid 100 g (0.215 mole), bromine 21.0 g (0.129 mole) and Freon 113 (500 ml) were mixed in the plastic reactor. The mixture was treated with fluorine in the same manner as described in Example 1. Approximately 1.7 fold excess fluorine was used, producing 92 grams of perfluorooctyl bromide (86% yield). Thus, using approximately half the amount of bromine as used in Example 1 produced a lower yield of the perfluoroalkyl halide.

EXAMPLE 3—Preparation of Perfluoroheptyl Bromide

Perfluorooctanoic acid 286 g (0.691 mole), bromine 55.3 g (0.345 mole) and Freon 113 (200 ml) were treated with fluorine (40 cc/min) at 30°– 37° C. When approximately 0.42 mole of fluorine was used, the solution turned from dark red to orange. Perfluorooctanoic acid 500 g (1.208 mole) and bromine 112 g (0.700 mole) were added to the reaction mixture. The mixture was again treated with fluorine until the color of bromine disappeared (about 0.83 mole of additional fluorine was used). The reaction mixture was poured into dilute hydrochloric acid and the precipitated solid comprising unreacted perfluorooctanoic acid (about 115 grams) was recovered. The organic phase was then separated, washed with water containing some sodium thiosulfite, and dried over magnesium sulfate. Fractional distillation of the precipitate produced 697 g of perfluoroheptyl bromide (96% yield based on the amount of acid reacted), having a boiling point of 118° C.

EXAMPLE 4—Preparation of Perfluorononyl Bromide

Perfluorodecanoic acid 788 g (1.53 mole), bromine 144 g (0.90 mole) and Freon 113 (200 ml) were treated with fluorine at 30°–38° C. according to the method of Example 3. Approximately 736 g of perfluorononyl bromide (88% yield) was produced. The perfluoroalkyl halide has a boiling point between 95°-6° C./20 mm Hg and a melting point of 30° C.

EXAMPLE 5—Preparation of Perfluoroundecyl Bromide

Perfluorododecanoic acid 404 g (0.565 mole), bromine 49.4 g (0.309 mole) and Freon 113 (400 ml) were treated with fluorine at 30°–37° C. The reaction mixture was poured into 2N hydrochloric acid (500 ml) and the freon solvent was directly distilled off from the mixture. The residue was cooled and the precipitated solids were collected through known filtration techniques. The precipitate was then distilled under vacuum, to give pure perfluoroundecyl bromide 401 g (95% yield). The bromide has a boiling point of 105° C./2 mm Hg and a melting point of 96°–98° C.

EXAMPLE 6—Preparation of Perfluoroheptyl Bromide

Perfluorooctanoic acid 300 g (0.724 mole), bromine 72.0 g (0.453 mole) and perfluoroheptyl bromide (640 g) were mixed and treated with fluorine at 30°–38° C. until the solution turned from dark red to yellow. The reaction mixture was poured into dilute hydrochloric acid and the precipitated unreacted acids were filtered off, producing 47 g of unreacted perfluorooctanoic acid. The organic layer was then dried over magnesium sulfate and distilled to produce perfluoroheptyl bromide 867 g (95% yield based on the amount of the acid reacted).

EXAMPLE 7—Preparation of Perfluoro(decahydro-1-naphtyl) Bromide

Perfluoro(decahydro-1-naphthoic) acid 46 g (0.094 mole), bromine 8.3 g (0.052 mole) and Freon 113 (200 ml) were mixed and treated with fluorine to give 45 g (92% yield) of perfluoro(decahydro-1-naphtyl bromide) after distillation. The perfluoroalkyl halide has a boiling point of 190° C.

EXAMPLE 8—Preparation of Perfluoro(2,5,8-trioxadecyl) Bromide

Perfluoro(3,6,9-trioxaundecanoic) acid 87 g (0.188 mole), bromine 16.5 g (0.103 mole) and Freon 113 (250 ml) were treated with fluorine at 30°–35° C. The reaction was terminated when the color of the solution turned from dark red to light red. Approximately 0.22 mole of fluorine was used. The mixture was poured into water and the organic phase was washed with sodium thiosulfite solution and then dried over magnesium sulfate. A fractional distillation of the organic phase gave 49 g of perfluoro(2,5,8-trioxadecyl bromide) (53% yield) having a boiling point of 109° C.

EXAMPLE 9—Preparation of Perfluoro-1,4-dibromobutane

Perfluoro-1,6-hexanedioic acid 800 g (2.76 mole), bromine 618 g (3.86 mole) and Freon 113 (300 ml) were mixed and treated with fluorine at 35°–39° C. according to the foregoing methods until the solution turned from dark red to light yellow. The product was then distilled to give 903 g of perfluoro-1,4-dibromobutane (91% yield) having a boiling point of 95° C.

EXAMPLE 10—Preparation of Perfluoro(1,11-dibromo-3,6,9-trioxa-undecane)

Perfluoro(4,7,10-trioxatridecane-1,1,3-dioic) acid 65 g (0.121 mole), bromine 21.2 g (0.133 mole) and Freon 113 (400 ml) were treated with fluorine at 30°–35° C. until the solution turned from dark red to light yellow. The reaction mixture was poured into water and the organic phase was separated and washed with sodium thiosulfite and dried over magnesium sulfate. After removing the solvent, the residue was vacuum distilled to give pure perfluoro(1,11-dibromo-3,6,9-trioxa- undecane) 64 g (88% yield), which had a boiling point of 63° C./16 mm Hg.

EXAMPLE 11—Preparation of Perfluoro(1-bromo-2,6-dimethylheptane)

Perfluoro(3,7-dimethylheptanoic) acid 543 g (1.506 mole), bromine 110 g (0.686 mole) and Freon 113 (200 ml) were treated with fluorine at 30°–37° C. until the solution turned from dark red to light yellow. 401 g (95% yield based on the amount of the acid reacted) of perfluoro(1-bromo-2, 6-dimethylheptane) was isolated after distillation. The product had a boiling point of 155° C., and 148 g of the unreacted acid was recovered as a distillation residue.

EXAMPLE 12—Preparation of Perfluoroheptyl Bromide

Perfluorooctanoic acid 18.6 g (0.045 mole), 48% hydrobromic acid 9.1 g (0.054 mole) and Freon 113 (400 ml) were mixed and treated with fluorine. The solution immediately turned to dark red. When the dark red color disappeared, fluorine was terminated and the reaction mixture was poured into dilute hydrochloric acid solution. The lower phase was separated and dried over magnesium sulfate. After removing the solvent, 7.2 g (36% yield) of perfluoroheptyl bromide was obtained.

EXAMPLE 13—Preparation of Perfluorohexyl Iodide

Perfluoroheptanoic acid 9.5 g (0.026 mole), iodine 4.0 g (0.016 mole) and Freon 113 (500 ml) were mixed and treated with approximately 33% fluorine diluted with nitrogen until the color due to iodine disappeared. The mixture was washed with water containing a small amount of sodium thiosulfite and dried over magnesium sulfate. 1.5 g (13% yield) of perfluorohexyl iodide was obtained.

Equivalents

Those skilled in the art will recognize, or be able to ascertain using no more than routine experimentation, many equivalents to the specific embodiments of the invention described herein. Such equivalents are intended to be encompassed by the following claims.

I claim:

1. A method of producing a perfluorocarbon halide, comprising:
   providing a perfluorocarbon acid;
   contacting the perfluorocarbon acid with a first halogenating agent in the presence of a second halogen which drives the reaction such that a perfluorocarbon halide is formed.

2. The method of claim 1 wherein the perfluorocarbon acid is a perfluorocarboxylic acid.

3. The method of claim 1 wherein the perfluorocarbon acid is a perfluoroalkane polyacid.

4. The method of claim 1 wherein the first halogenating agent is selected from the group
   consisting of bromine, iodine, chlorine, hydrobromic acid, hydrochloric acid, potassium bromide, potassium iodide, potassium chloride, trimethylsilyl iodide, trimethylsilyl chloride, fluorocarbons, and chlorofluoroethers.

5. The method of claim 1 wherein the second halogen drives the reaction by forming a strong hydrogen bond with hydrogen released from an acid group.

6. The method of claim 1 wherein the second halogen is selected from the group consisting of fluorine, chlorine, bromine, and iodine.

7. The method of claim 1 wherein the first halogenating agent is a brominating agent and the second halogen is elemental fluorine.

8. The method of claim 1 wherein a perfluorocarbon hypohalite is directly formed prior to the formation of the perfluorocarbon halide.

9. The method of claim 1 wherein the perfluorocarbon halide is formed in a one-pot reaction.

10. The method of claim 1 wherein the perfluorocarbon acid and the first halogenating agent are dissolved in a solvent prior to the step of introducing the second halogen and wherein the second halogen is insoluble in the solvent.

11. The method of claim 1 wherein the perfluorocarbon acid has a formula as follows:

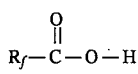

wherein $R_f$ is a perhalogenated moiety.

12. The method of claim 11 wherein the perfluorocarbon acid is selected from the group consisting of perfluorononanoic acid, perfluorooctanoic acid, perfluorodecanoic acid, perfluorododecanoic acid, perfluoro(decahydro-1-naphthoic) acid, perfluoro(3,6,9-trioxaundecanoic) acid, perfluoro-1,6-hexanedioic acid, perfluoro(4,7,10-trioxatridecane-1,1,3-dioic) acid, perfluoro(3,7-dimethylheptanoic) acid, and perfluoroheptanoic acid.

13. The method of claim 1 wherein the first halogenating agent is selected from the group consisting of bromine, iodine, chlorine, hydrobromic acid, hydrochloric acid, potassium bromide, potassium iodide, potassium chloride, trimethylsilyl iodide, trimethylsilyl chloride, fluorocarbons, and chlorofluoroethers.

14. The method of claim 1 wherein the halogenating agent is bromine.

15. The method of claim 1 wherein the perfluorocarbon halide is selected from the group consisting of perfluorocarbon bromides, perfluorocarbon iodides, perfluorocarbon polybromides and perfluorocarbon polyiodides.

16. The method of claim 1 wherein the perfluorocarbon halide is a perfluorocarbon bromide.

17. The method of claim 1 wherein the perfluorocarbon halide is a perfluorocarbon iodide.

18. The method of claim 1 wherein the perfluorocarbon halide is formed at a temperature between about −20° C. and about 100° C.

19. The method of claim 18 wherein the perfluorocarbon halide is formed at a temperature between about 0° C. and about 50° C.

20. A method of producing a perfluoroalkyl halide comprising:

providing a perfluorocarbon acid and a first halogenating agent, pre-mixing a second halogen and a diluent together forming a premixture, and introducing the premixture to the perfluorocarbon acid and the first halogenating agent to form a reaction amalgam such that a perfluoroalkyl halide is formed in a single step reaction.

21. A method of producing a perfluoroalkyl halide comprising:

providing a perfluorocarbon acid and a first halogenating agent, dissolving the perfluorocarbon acid and the halogenating agent in a solvent, pre-mixing a halogen and a diluent together forming a premixture, introducing the pre-mixture to the dissolved perfluorocarbon acid and halogenating agent, and performing the reaction at a temperature between about −20° C. and about 100° C. such that a perfluoroalkyl halide is formed in a single step reaction.

22. A method of producing a perfluoroalkyl halide comprising:

providing a pre-mixture of a perfluorocarbon acid and a first halogenating agent forming a premixture, and introducing a second halogen to the pre-mixture to directly form a perfluoroalkyl hypohalite prior to forming the perfluoroalkyl halide.

23. A method for producing a perfluorocarbon hypohalite directly from perfluorcarbon acids, comprising:

providing a perfluorocarbon acid; and contacting the perfluorocarbon acid with a halogenating agent in the presence of elemental fluorine such that a perfluorocarbon hypohalite is directly formed.

24. Perfluorocarbon halides produced by the method of claims 1, 20, 21 or 23.

* * * * *